United States Patent
Ha et al.

(10) Patent No.: US 9,597,445 B2
(45) Date of Patent: Mar. 21, 2017

(54) FLUID MANAGEMENT SYSTEM FOR USE IN A MEDICAL PROCEDURE

(75) Inventors: Catherine P. Ha, Westminster, CA (US); Wayne S. Wong, Irvine, CA (US); Michael J. Claus, Newport Coast, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 400 days.

(21) Appl. No.: 13/294,705

(22) Filed: Nov. 11, 2011

(65) Prior Publication Data

US 2013/0123680 A1    May 16, 2013

(51) Int. Cl.
*A61F 9/007*  (2006.01)
*A61M 3/02*  (2006.01)

(52) U.S. Cl.
CPC ....... *A61M 3/0241* (2013.01); *A61F 9/00745* (2013.01); *A61M 3/022* (2014.02); *A61B 2218/002* (2013.01); *A61M 2210/0612* (2013.01)

(58) Field of Classification Search
CPC .... A61M 1/005; A61M 3/022; A61M 3/0229; A61M 3/0241; A61M 5/16818; A61M 5/168; A61M 5/16804; A61M 2210/0612; A61M 2205/3331; A61F 9/00745; A61F 9/00736; A61B 2218/002
See application file for complete search history.

(56) References Cited

U.S. PATENT DOCUMENTS

| | | | | |
|---|---|---|---|---|
| 5,112,019 A * | 5/1992 | Metzler | ............... | A61M 3/0241 248/125.2 |
| 5,810,765 A * | 9/1998 | Oda | .................... | A61M 1/0058 604/22 |
| 6,024,720 A * | 2/2000 | Chandler | ............ | A61M 1/0058 604/35 |
| 6,149,621 A * | 11/2000 | Makihara | ............ | A61M 1/0058 417/477.3 |
| 6,283,937 B1 * | 9/2001 | Takamatsu | .......... | A61M 1/0031 604/31 |
| 2002/0085952 A1 * | 7/2002 | Ellingboe | ........... | A61M 1/3621 422/45 |
| 2004/0116846 A1 * | 6/2004 | Olivera | ............... | A61M 3/0241 604/36 |

(Continued)

*Primary Examiner* — Bhisma Mehta
*Assistant Examiner* — Jenna Zhang
(74) *Attorney, Agent, or Firm* — Abbott Medical Optics Inc.

(57) ABSTRACT

An apparatus and method for controlling fluid flow provided by an apparatus to a patient's eye during a surgical procedure. The method includes automatically adjusting an irrigation fluid source to a predetermined height during the surgical procedure using the apparatus, receiving a request either that the irrigation fluid source be moved to a different height from the predetermined height or that a manual adjustment mode be entered, and ceasing automatic adjusting and requiring manual adjustment of the height of the irrigation fluid source until the surgical procedure is completed or an indication received to resume automatic height adjustment of the irrigation fluid source. As an alternative, fluid flow rate or intraocular pressure may be maintained, and the design may include making adjustments to default values in other modes based on the adjustment made.

26 Claims, 4 Drawing Sheets

(56) References Cited

U.S. PATENT DOCUMENTS

| | | | |
|---|---|---|---|
| 2006/0149301 A1* | 7/2006 | Claus | A61F 9/00745 606/169 |
| 2011/0054385 A1* | 3/2011 | Eichler | A61M 1/0058 604/22 |
| 2011/0112472 A1* | 5/2011 | Jacobson | A61F 9/00736 604/67 |

* cited by examiner

FLUID MANAGEMENT SYSTEM FOR USE IN A MEDICAL PROCEDURE

BACKGROUND

Field

The present invention relates generally to fluid management during a medical procedure and more specifically to automatic fluid management by adjusting height of an irrigation fluid source, such as a BSS (Balanced Salt Solution) bottle, during an ocular surgical procedure.

Background

Surgical systems, such as phacoemulsification systems for ophthalmic surgery, require fluid infusion while the surgery is being performed. Accurate management of such fluid infusion is critical to the procedure. In the phacoemulsification surgical context, the surgeon employs a phacoemulsification machine that controls fluid flow to the ocular region of the patient. If fluid flow is altered during a surgical procedure based on some external factor, such as switching submodes on the phacoemulsification machine, an adverse situation can develop, potentially causing severe damage to the patient.

Fluid flow is typically controlled during an ophthalmic or ocular surgical procedure by the phacoemulsification machine adjusting the height of an infusion bottle or other irrigation fluid source. Bottle height is typically controlled automatically, i.e. without user intervention, where the machine raising the bottle height results in more fluid pressure, and lowering bottle height results in less fluid pressure.

One issue with such an automatic height or flow adjustment arrangement is that default settings for bottle height may be provided in certain modes or submodes or under certain phacoemulsification machine settings. Any change in situations conditions, such as a change of mode or submode, can sometimes cause automatic operation to alter bottle height to an unacceptable level for the conditions encountered. Also, the surgeon may encounter circumstances that require an adjustment to bottle height, such as encountering a compromised eye during surgery. In this case, the ability to adjust bottle height, or override the machine settings, is highly desirable. A problem can arise if, after setting a height to a desired height, the conditions change and/or the machine moves the irrigation fluid source to an unwanted height. In the presence of a submode change, the surgeon may wish to employ a fluid flow rate that differs from the default setting for the new submode of the machine.

The end result of this uncertainty in bottle height is that the surgeon may need to monitor bottle height settings constantly, particularly during machine mode or submode changes. Such monitoring is undesirable as it takes the surgeon's attention away from the surgical procedure. Again, issues encountered during surgery can have devastating effects on the patient and must be avoided.

There is therefore a need in the art for techniques and devices that can provide efficient and effective bottle height management during a surgical procedure that reduces the need for the surgeon to devote his or her attention to bottle height and fluid flow conditions.

SUMMARY

An apparatus and method for controlling fluid flow provided by an apparatus to a patient's eye during a surgical procedure is provided. The method includes automatically adjusting an irrigation fluid source to a predetermined height during the surgical procedure using the apparatus, receiving a request either that the irrigation fluid source be moved to a different height from the predetermined height or that a manual adjustment mode be entered, and ceasing automatic adjusting and requiring manual adjustment of the height of the irrigation fluid source until the surgical procedure is completed or an indication received to resume automatic height adjustment of the irrigation fluid source. As an alternative, fluid flow rate or intraocular pressure may be maintained, and the design may include making adjustments to default values in other modes based on the adjustment made.

Other features and advantages of the present invention should be apparent from the following description of exemplary embodiments, which illustrate, by way of example, aspects of the invention.

DETAILED DESCRIPTION

One aspect of the present invention is the ability for a surgeon performing an ocular surgical procedure to override the automatic settings of the phacoemulsification machine, essentially setting the bottle height to a desired value at all times during the surgery. Rather than the automatic switching that occurs continually with existing phacoemulsification machines, the present design overrides the automated settings, such as by providing a manual mode for bottle height adjustment. In most cases, once a manual override mode is engaged, the machine stays on manual override for the remainder of the procedure.

Figure 1:
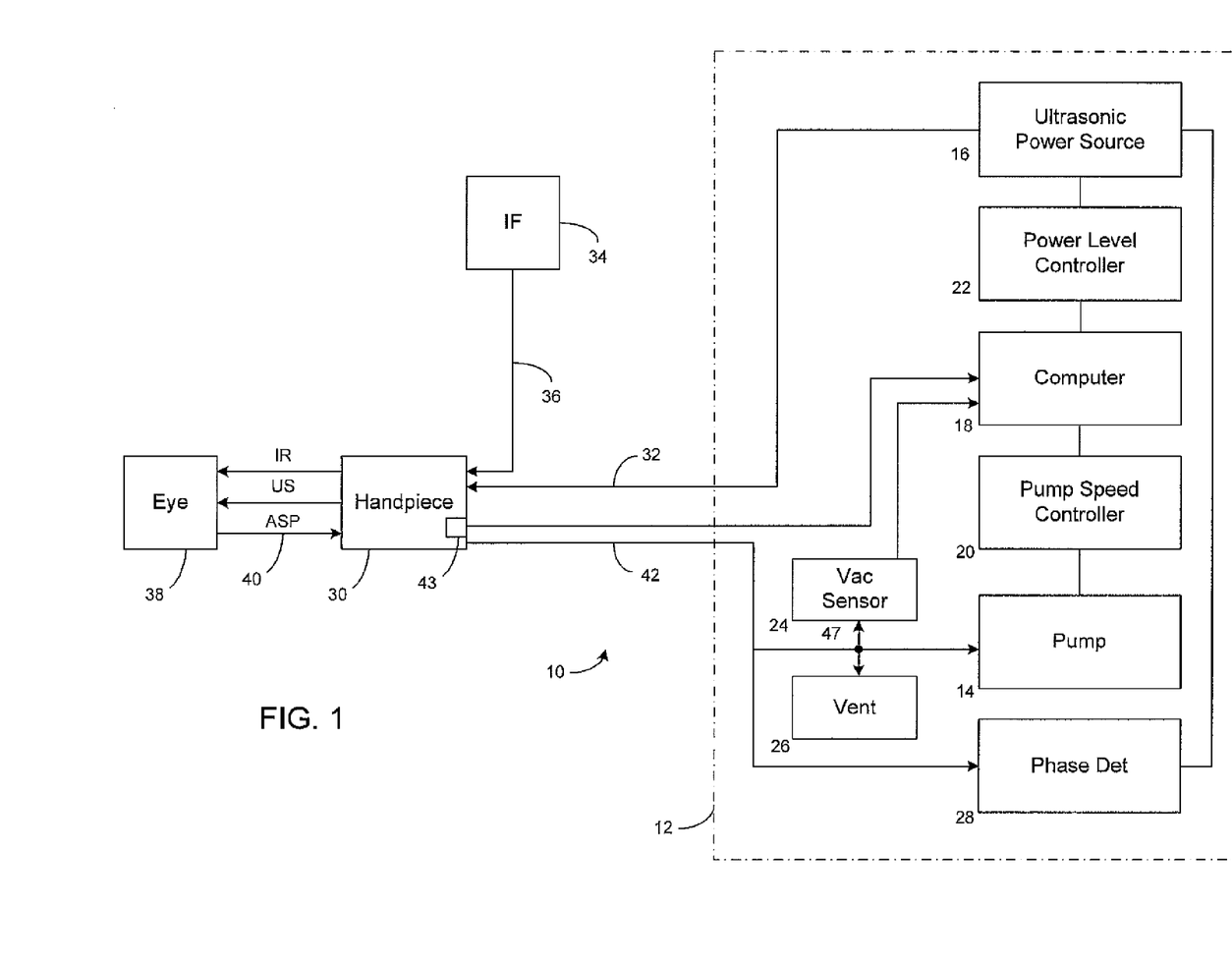
FIG. 1 illustrates a typical phacoemulsification system.

FIG. 1 illustrates a typical phacoemulsification system 10. The system includes a control unit 12, indicated by the dashed lines in FIG. 1 which includes a pump 14, a source of pulsed ultrasonic power 16, and a microprocessor computer 18 that provides control outputs to pump speed controller 20 and ultrasonic power level controller 22. Vacuum sensor 24 provides an input to computer 18 representing the vacuum level on the input side of pump 14 via line 47. System 10 may also have suitable venting provided by vent 26. Examples of pump 14 include a peristaltic pump, a Venturi pump, or both, but other types of pumps or combination of pumps may be employed.

Phase detector 28 provides an input to computer 18 representing a phase shift between a sine wave representation of the voltage applied to handpiece 30 and the resultant current into handpiece 30. The block representation of handpiece 30 includes a needle and electrical means, typically a piezoelectric crystal, for ultrasonically vibrating the needle. Control unit 12 supplies power on line 32 to phacoemulsification handpiece 30. An irrigation fluid source 34 is fluidly coupled to handpiece 30 through line 36. The irrigation fluid and ultrasonic power are applied by handpiece 30 to a patient's eye, or affected area or region, indicated diagrammatically by block 38, and may include a lumen (not shown). Alternatively, the irrigation source may be routed to eye 38 through a separate pathway independent of the handpiece. Eye 38 is aspirated by the pump 14 through line/handpiece needle 40 and line 42. Switch 43 disposed on handpiece 30 may be utilized as a means for enabling a surgeon/operator to select an amplitude of electrical pulses to the handpiece via computer 18, power level controller 22 and ultrasonic power source 16 as discussed herein. Any suitable input means, such as, for example, a foot pedal (not shown) may be utilized in lieu of switch 43.

Figure 2:
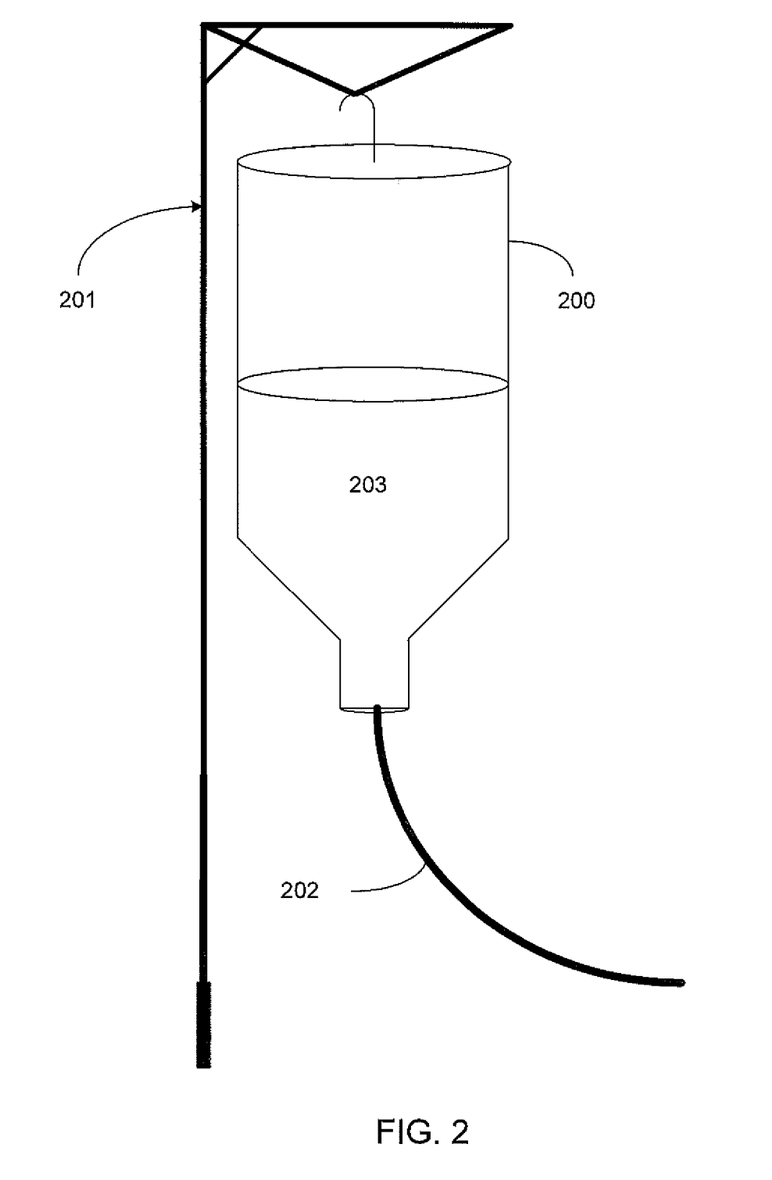
FIG. 2 is one example of an irrigation fluid source in the form of a BSS (balanced salt solution) bottle.

The term "irrigation fluid source" is used throughout this discussion and is intended to be interpreted a broadly as possible to include virtually anything that can deliver fluid to a patient, or more particularly, a patient's eye. In one embodiment, the irrigation fluid source may be any fluid source conveying fluid through phacoemulsification system 10 to the patient. In its most common form, irrigation fluid source 34 typically takes the form of infusion bottle 200 containing fluid 203, an example of which is shown in FIG. 2. Other irrigation fluid sources may be employed, such as a collapsible bag or other fluid maintaining device. The irrigation fluid source typically is placed on a device such as the retractable metal tube or tube arrangement 201 shown in FIG. 2 and controllable by control unit 12. In essence, control unit 12 commands the retractable metal tube or tube arrangement to extend or retract, thereby raising or lowering irrigation fluid source 34 (FIG. 1) or 200 (FIG. 2) and altering fluid flow through a line or tube such as line 202 in FIG. 2. However, as fluid flow is of paramount interest, any device that can control providing fluid to the patient is acceptable. As one alternative, fluid may be provided from a source such as a bottle or bag and may be controlled by restricting flow rather than altering height.

As previously noted, typical operation of phacoemulsification system 10 and control unit 12 is to automatically raise and lower irrigation fluid source 34 depending on circumstances encountered. Phacoemulsification system 10 may enter different submodes, such as a vitrectomy submode, to perform different surgical procedures. New submodes may be added and offered by the manufacturer as desired. Typical operation has been for the phacoemulsification system to maintain a set of desired bottle heights, or irrigation fluid source heights, depending on the submode and the need for fluid when performing a surgical procedure in the particular submode. As an example, when in the vitrectomy submode, a certain desired bottle/irrigation fluid source height may be set, while when switching out of vitrectomy mode to a standard phacoemulsification mode the bottle/irrigation fluid source height may automatically adjust to a different value.

The problem with automatic operation is the condition wherein a different setting is desired than the default setting. Each submode is typically provided with a desired height for irrigation fluid source 34, and upon entering the submode, whether automatically or manually, the phacoemulsification system raises or lowers irrigation fluid source 34 to the desired height. Such operation is acceptable for many situations. However, in those cases where special circumstances arise requiring greater or lesser fluid flow, this automatic operation to specific setpoints can be problematic. Such circumstances can include an eye having an unsound structure or an eye that has been compromised. In these situations, not only must the surgeon initially set the height of irrigation fluid source 34 to the desired height upon entering a submode with a height setpoint that is not optimal for the situation, but upon transitioning to a subsequent submode, either manually or automatically, the surgeon must then again set the height to the desired height.

Figure 3:
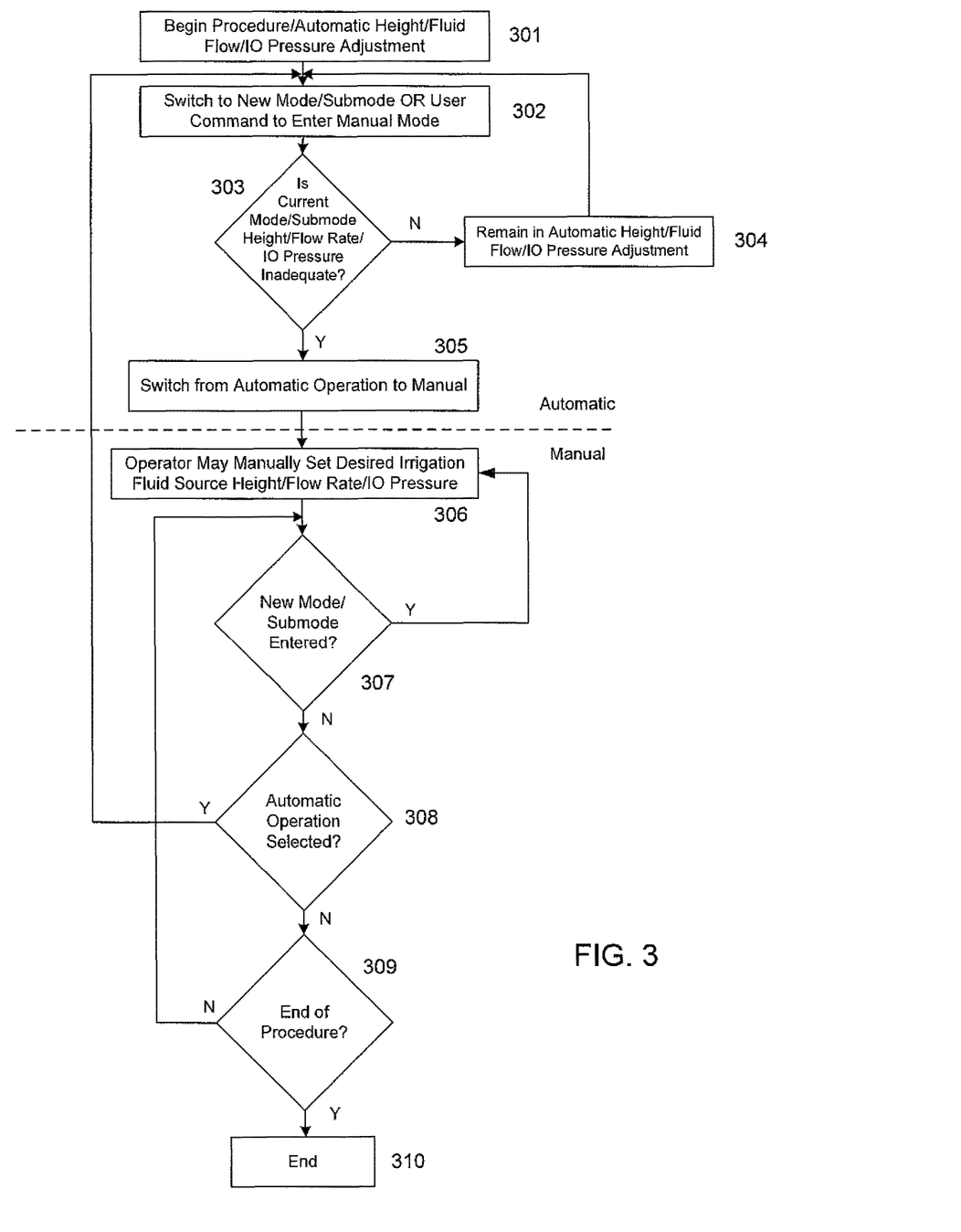
FIG. 3 shows a flowchart of operation of one embodiment of the present design.

The present design enables the surgeon to modify the automatic procedure. As shown in FIG. 3, automatic operation is initially enabled at point 301, wherein phacoemulsification system 10 is operating and switching between submodes as commanded or is automatically adjusting height, fluid flow rate, or intraocular pressure (IOP). At point 302, phacoemulsification system 10 switches into a new mode or submode, either automatically or based on user prompt. The surgeon or other operating personnel determines whether the default height setting for irrigation fluid source 34 is inappropriate for the condition encountered at point 303. If the default height setting is adequate, i.e. the answer to the question at point 303 is no (N), then the system 10 will remain in automatic height/fluid flow/intraocular pressure adjustment mode at point 304. If the default height setting is inadequate, i.e. the answer to the question at point 303 is yes (Y), the surgeon or other operating room personnel then switches the system from automatic irrigation fluid source height management to manual irrigation fluid source height management at point 305. If the surgery never enters manual fluid flow/height management, i.e. never crosses the dotted line in FIG. 3 from Automatic to Manual, automatic operation continues until the surgical procedure ends or the phacoemulsification machine is turned off.

At point 306, surgery continues, and operating room personnel can manually adjust the flow rate or height of the irrigation fluid source, or adjust to obtain a desired intraocular pressure (IOP). The system determines whether a new mode or submode has been entered at point 307. If so, the operator may manually adjust or readjust the flow rate or height of irrigation fluid source 34 to the desired flow rate, height, or IOP. If not, the system determines at point 308 whether automatic operation has been selected, i.e. a desire to return to automatic fluid flow/height management. If so, operation progresses to point 302. If automatic operation is not selected, the system determines whether the procedure has ended at point 309, typically either by an indication of such, a determination that the procedure has ended (e.g. no further fluid has been requested), or the machine has been turned off, collectively shown as end point 310. If the procedure has not ended at point 309, operation continues in manual mode beginning at point 307.

One example of the present design is a surgical procedure wherein the eye capsule is compromised and vitrectomy is needed. The surgeon changes phacoemulsification system 10 through control unit 12 to the vitrectomy submode to perform a vitrectomy procedure. The surgeon may also switch using control unit 12 to an irrigation/aspiration mode to clean the remnants of the vitrectomy procedure. However, before switching from the vitrectomy mode, the surgeon may be prompted by control unit 12 or may enter a command via control unit 12 making fluid flow/height or IOP adjustment manual for the remainder of the vitrectomy procedure. If the surgeon elects either of these modes, the remainder of the procedure—even if switched from the vitrectomy mode or submode—maintains the manual fluid flow/height or IOP adjustment. The surgeon can then complete the remainder of the procedure without introducing unwanted pressure into the eye. Note that as an alternative, the surgeon can make IOP a fixed value and height will adjust accordingly. In other words, the surgeon may manually lower the irrigation fluid source, but elect to automatically maintain the IOP.

Another example of operation of the present design is the surgeon noting mid-procedure that the patient's eye structure is unsound. Realizing that such a condition requires lower fluid pressure to the eye, the surgeon commands, via control unit 12, to lower the pressure by lowering the height of the irrigation fluid source. The surgeon may then be prompted as to whether she wishes to make the irrigation fluid source height a manual setting, or wishes to maintain the current IOP setting. If so, the remainder of the surgical procedure occurs with a manual setting for irrigation fluid source height, fluid flow rate, or IOP value, meaning in the case of a constant height, the irrigation fluid source remains at the initially set position unless commanded otherwise by the surgeon or other personnel. In the case of manual fluid flow rate or IOP value, the height may adjust to retain a constant fluid flow rate or IOP value.

As an alternative to the foregoing, the machine may remain in automatic mode but may alter height, flow parameter, or IOP based on adjustments made by the operating room personnel. For example, the device may have a default set of height values for various machine modes, such as phaco mode 1—25 percent of full irrigation fluid source height, phaco mode 2—50 percent, phaco mode 3—75 percent, and phaco mode 4—100 percent. If the surgeon is in phaco mode 2 and adjusts the height down 15 percent, the device may, upon switching to another mode, decrease the height for all phaco modes by 15 percent, i.e. mode 1—10 percent, mode 2—35 percent, mode 3—60 percent, mode 4—85 percent. Such adjustments based on mode may also be made in the case of maintaining desired fluid flow or IOP values, that is, an increase or decrease to all modes based on a manual adjustment provided by the operating room personnel. Such an adjustment may be made via graphical user interface, such as the surgeon requesting a decrease in flow rate from X ml/sec to X−Y ml/sec. In this case, the system would seek to maintain a flow rate of X−Y while in the current mode and decrease all other mode flow rates by Y. An automatic switch to another mode would result in a change to the flow rate for that mode minus Y ml/sec.

The system may adjust the height of the irrigation fluid source based on input received from the surgeon via a foot pedal switch, selection from the GUI, or other available user input device. The selecting mechanism may provide for returning to automatic operation during the procedure. In this manner, the surgeon may toggle the setting between automatic and manual operation in the event of a problem arising during the surgical procedure.

As may be appreciated, the present design may be employed in control unit 12 of phacoemulsification system 10 as software or hardware changeable by surgeon or other personnel. Such functionality may be provided at control unit 12 including components such as an independent graphical user interface (GUI) module, an instrument host module, and a controller module, such as a foot switch, to control the phacoemulsification system. The graphical user interface module may include a touchscreen or a series of buttons adjacent to a screen, or a computer keyboard or other suitable input device wherein the surgeon or user can input information, such as desired flow rate or irrigation fluid source height. If desired fluid rate is provided, control unit 12 via one of its components may determine the appropriate irrigation fluid source height. Alternately, the control unit may be programmed to prompt the surgeon or user when particular events occur. For example, if control unit 12 is operating with automatic fluid flow/irrigation fluid source height operation and the user requests switching to a particular mode or submode, the surgeon or user may be prompted as to whether he wishes to keep the irrigation fluid source at the current height. He may respond by selecting "yes" or "no" when prompted by the GUI module.

In another example, the surgeon may be prompted as to whether she wishes to make the irrigation fluid source height an automatic setting based on IOP. The system may monitor the intraocular pressure and automatically adjust the bottle height as required to realize a set pressure within the eye. Methods for measuring and monitoring the intraocular pressure throughout the procedure are generally known by persons skilled in the art. The remainder of the surgical procedure occurs with the system automatically making irrigation fluid source height adjustments to maintain the current IOP.

As an alternative, the present design may include an ability for operating room personnel to adjust the irrigation fluid source up or down by a predetermined amount for each of the default values in each of the modes. In a previous example, the settings of 25 percent, 50 percent, 75 percent, and 100 percent were given for modes phaco 1, phaco 2, phaco 3 and phaco 4, respectively. The surgeon may enter a decrease of 10 percent for all settings via the GUI, at which time phaco mode 1 would be adjusted to 15 percent, phaco 2 to 40 percent, phaco 3 to 65 percent, and phaco 4 to 90 percent. This differs from the foregoing arrangement in that rather than an adjustment calculated by the phaco machine for the adjusted setting in one mode, the present design enables the operating room personnel to enter the adjustment amount only, applicable to all or selected modes, irrespective of current mode or setting.

In each of these modes wherein adjustment is made to values in multiple modes at once, the irrigation fluid source heights or IOPs or flow rates may be stored as relative values. Assuming a manual setting of irrigation fluid source height, the value of each mode may be commanded to increase or decrease irrigation fluid source height by a value X, where X represents the initial change in height. In this context, values above 100 percent are set at 100 percent, and values below zero are set to zero, where 100 percent represents a highest height and zero a lowest height (and not necessarily zero inches, etc.) These may be converted from inches, and the other values (IOP and flow rate) may entail a calculation or conversion to a particular height. As may be appreciated, if pressure or fluid flow change during the procedure while, for example, in a single mode, the system may adjust the height to achieve the desired IOP or flow rate.

One additional embodiment of the present design includes providing an ability, via the GUI, or a button, or any other user interface, to switch the phacoemulsification machine from automatic to manual, e.g. the surgeon simply stops automatic operation altogether. This can also be reversed, namely the user can switch the machine from manual to automatic if resumption of automatic operation is desired. This is an alternative to manual height adjustment via the user interface, for example, in that the user does not have to adjust irrigation fluid source height, such as via the GUI, to exit the automatic mode and enter the manual mode. The alternative is to simply provide a switch such that manual height adjustment is not required.

Figure 4:
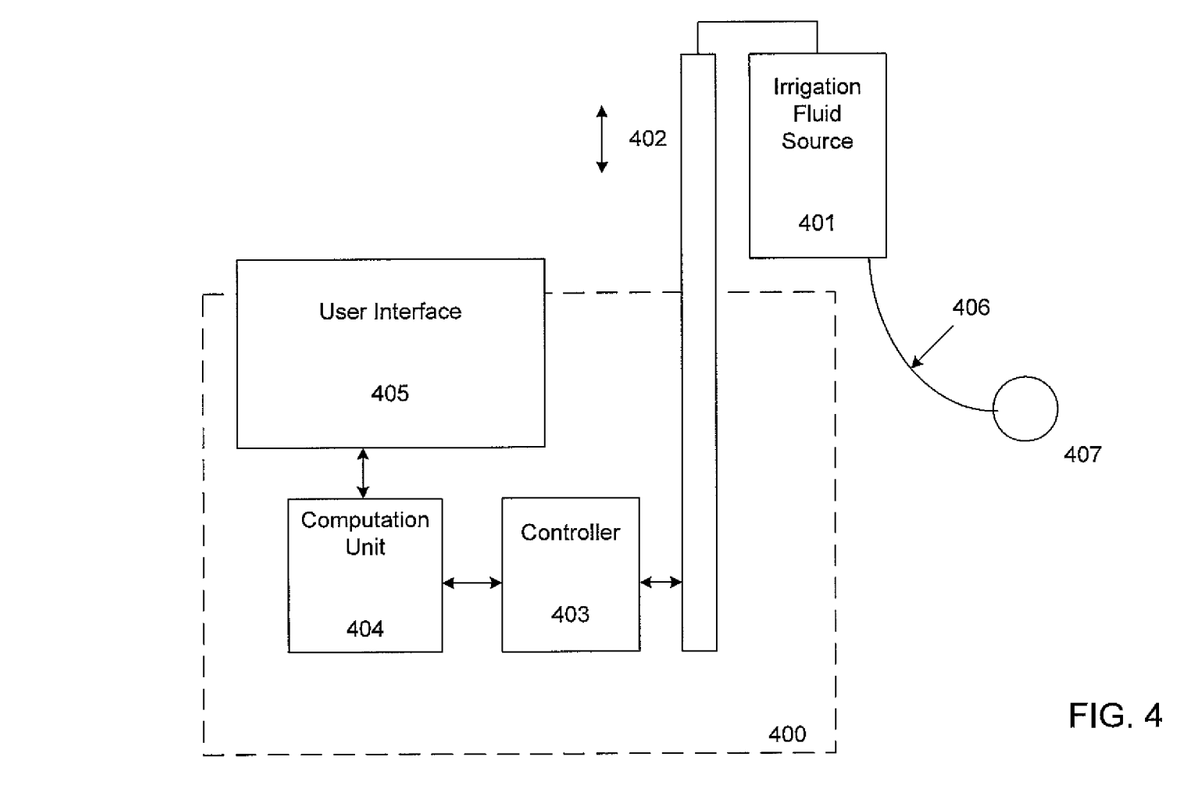
FIG. 4 is a basic schematic of the components of one embodiment of the present design.

FIG. 4 illustrates a schematic of the basic components of the present design. From FIG. 4, there is shown an irrigation fluid source 401 suspended at a first height using retractable tubular arrangement 402, which may be extended or retracted to change height, and tubing 406 connecting the irrigation fluid source 401 with eye 407. The retractable tubular arrangement is operated by controller 403. Controller 403 interfaces with a processor or computation unit 404, typically located inside ocular surgical device 400. The processor or computation unit 404 may receive indications, either from the user via user interface 405 or internally via mode change or other operation. Internally in this context means that the processor or computation unit 404 or some component of ocular surgical device 400 initiates a change, such as a mode change or a submode change, and as a result the device provides an indication to the processor or computation unit 404 either a different flow rate or different height request. The processor may make such computation and provide the height change indication itself, or external conditions outside the processor or computation unit 404 but inside ocular surgical device 400 may cause a component to transmit an indication to the processor or computation unit 404 to change height. Thus the indication may be provided by the user, such as via user interface 405 in communication with ocular surgical device 400, or may be provided by any component within the ocular surgical device to the processor or computation unit.

Programming of such operation of the present design may be fairly straightforward. Upon entering desired modes, the user may be prompted as to whether he or she wishes to keep the irrigation fluid source at its current height. Automatic operation may continue uninterrupted until the user requests, using a series of commands, button pushes, typed commands, etc. that he wishes to alter the flow rate and/or irrigation fluid source height.

Those of skill in the art will recognize that the step of a method described in connection with an embodiment may be interchanged without departing from the scope of the invention.

Those of skill in the art would also understand that information and signals may be represented using any of a variety of different technologies and techniques. For example, data, data packets, packet groups, instructions, commands, information, signals, and bits that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for controlling fluid flow provided by an apparatus to a patient's eye during a surgical procedure, comprising:
   automatically adjusting an irrigation fluid source to a predetermined height during the surgical procedure;
   receiving a request that the irrigation fluid source be moved to a different height from the predetermined height; and
   on a condition that the different height is determined to be inappropriate:
      ceasing the automatic adjusting of the irrigation fluid source at the predetermined height while the fluid continues to flow to the patient's eye,
      preventing further automatic adjusting of the irrigation fluid source away from the predetermined height, and
      allowing only manual adjustment of the irrigation fluid source height to adjust the flow rate of said fluid which continues to flow to the patient's eye, until the surgical procedure is completed or until an indication to resume automatic height adjustment of the irrigation fluid source is received.

2. The method of claim 1, wherein the receiving the request comprises receiving a request from a user.

3. The method of claim 2, wherein receiving the request occurs via a user interface provided at the apparatus.

4. The method of claim 1, wherein the receiving the request comprises receiving a request to enter a manual mode.

5. The method of claim 1, wherein the receiving the request comprises receiving a request to maintain an intraocular pressure (IOP) or fluid flow rate, and the method further comprises determining a height adjustment based on the IOP or the fluid flow rate.

6. The method of claim 1, further comprising:
   adjusting a default height related value for at least one other mode based on a difference between the predetermined height and the different height.

7. The method of claim 6, wherein the default height related value is an irrigation fluid source height, an intraocular pressure (IOP) or a fluid flow rate.

8. The method of claim 1, wherein the receiving the request comprises receiving the request as a result of changing modes from a first operating mode indicating a first desired height to a second operating mode indicating a second desired height, wherein the first desired height and the second desired height are different.

9. The method of claim 1, wherein the apparatus is a phacoemulsification machine and the surgical procedure is an ocular surgical procedure.

10. The method of claim 1, wherein the indication to resume automatic adjustment comprises a user entered indication provided via a user interface.

11. The method of claim 1, wherein the predetermined height is a first height provided for a first mode and the different height is a second default height provided for a second mode.

12. An apparatus configured to provide fluid from an irrigation fluid source during a surgical procedure, comprising:
a retractable tubular arrangement configured to maintain the irrigation fluid source at a desired height;
a controller configured to automatically adjust the irrigation fluid source using the retractable tubular arrangement to a predetermined height during the surgical procedure; and
a processor configured to receive a request that the irrigation fluid source be moved to a different height from the predetermined height and on a condition that it is determined that the different height is inappropriate, the processor further configured to command the controller to:
cease the automatic adjusting of the irrigation fluid source at the predetermined height while the fluid continues to flow during the surgical procedure,
prevent further automatic adjusting of the irrigation fluid source away from the predetermined height, and
allow only manual adjustment of the irrigation fluid source height to adjust the flow rate of said fluid which continues to flow during the surgical procedure, until the surgical procedure is completed or until an indication is received to resume automatic adjustment of height of the irrigation fluid source.

13. The apparatus of claim 12, wherein the processor is further configured to receive the indication from a user.

14. The apparatus of claim 13, wherein the processor receives the indication from a user interface.

15. The apparatus of claim 12, wherein the processor receives the request as a result of the apparatus changing modes from a first operating mode indicating a first desired height to a second operating mode indicating a second desired height, wherein the first desired height and the second desired height are different.

16. The apparatus of claim 12, wherein the apparatus is a phacoemulsification machine and the surgical procedure is an ocular surgical procedure.

17. The apparatus of claim 12, further comprising:
a user interface, wherein the indication to resume automatic adjustment is entered via the user interface by a user.

18. The apparatus of claim 12, wherein the predetermined height is a first default height provided for a first mode of the apparatus and the different height is a second default height provided for a second mode of the apparatus.

19. A method for controlling fluid flow to a patient's eye using an ocular surgical device during an ocular surgical procedure, comprising:
automatically positioning an irrigation fluid source at a first desired height via the ocular surgical device without operator intervention during the ocular surgical procedure;
requesting the ocular surgical device move the irrigation fluid source to a different height from the first desired height; and
on a condition that the different height is determined to be inappropriate:
ceasing the automatic positioning of the irrigation fluid source without operator intervention at the predetermined height while the fluid continues to flow to the patient's eye,
preventing further automatic adjusting of the irrigation fluid source away from the predetermined height, and
allowing only manual adjustment of the irrigation fluid source height to adjust the flow rate of said fluid which continues to flow to the patient's eye, until the surgical procedure is completed or until an indication is received to resume automatic height adjustment without operator intervention of the irrigation fluid source.

20. The method of claim 19, wherein the requesting comprises a user providing a request to the ocular surgical device for the different height.

21. The method of claim 20, wherein the requesting occurs via a user interface provided at the ocular surgical device.

22. The method of claim 19, wherein the requesting comprises the ocular surgical device providing an internal indication upon changing modes from a first operating mode indicating the first desired height to a second operating mode indicating the different height.

23. The method of claim 19, wherein the ocular surgical device is a phacoemulsification machine.

24. The method of claim 19, wherein the indication to resume height adjustment without operator intervention comprises a user entered indication provided via a user interface.

25. The method of claim 19, wherein the first desired height comprises a first default height provided for a first mode of the ocular surgical device and the different height comprises a second default height provided for a second mode of the ocular surgical device.

26. A method for controlling fluid flow provided by an apparatus to a patient's eye during a surgical procedure, comprising:
automatically adjusting an irrigation fluid source to a predetermined height during the surgical procedure; and
on a condition that the predetermined height is determined to be inappropriate:
receiving a request that a manual adjustment mode be entered,
ceasing the automatic adjusting of the irrigation height at the predetermined height while the fluid continues to flow to the patient's eye,
preventing further automatic adjustment of the irrigation height away from the predetermined height, and
allowing only manual adjustment of the irrigation fluid source height to adjust the flow rate of said fluid which continues to flow to the patient's eye, until the surgical procedure is completed or until an indication is received to resume automatic height adjustment of the irrigation fluid source.

\* \* \* \* \*